United States Patent [19]

Quagliato et al.

[11] Patent Number: 4,925,839

[45] Date of Patent: May 15, 1990

[54] ANTIHYPERTENSIVE BENZOPYRAN DERIVATIVES

[75] Inventors: Dominick A. Quagliato; Leslie G. Humber, both of North Brunswick, N.J.

[73] Assignee: American Home Products Corporation, New York, N.Y.

[21] Appl. No.: 210,970

[22] Filed: Jun. 24, 1988

Related U.S. Application Data

[63] Continuation-in-part of Ser. No. 146,875, Jan. 22, 1988, abandoned.

[30] Foreign Application Priority Data

Oct. 27, 1987 [CA] Canada ................................. 550349

[51] Int. Cl.$^5$ .................. A61K 31/445; C07D 405/04
[52] U.S. Cl. ................................. 514/212; 514/309; 514/320; 514/414; 514/422; 514/456; 540/451; 540/480; 540/524; 540/596; 546/141; 546/196; 548/454; 548/525; 549/399
[58] Field of Search ............... 548/454, 525; 514/414, 514/422, 212, 309, 320, 456; 549/399; 540/596, 480, 451, 524; 546/196, 141

[56] References Cited

U.S. PATENT DOCUMENTS

| | | | |
|---|---|---|---|
| 4,048,317 | 9/1977 | Watts | 514/422 |
| 4,179,510 | 12/1979 | McCall | 514/456 |
| 4,280,988 | 7/1981 | Franckowiak et al. | 514/247 |
| 4,285,955 | 8/1981 | Wehinger et al. | 546/258 |
| 4,542,149 | 9/1985 | Evans et al. | 514/422 |
| 4,616,021 | 10/1986 | Ashwood et al. | 514/414 |

FOREIGN PATENT DOCUMENTS

| | | | |
|---|---|---|---|
| 126311 | 11/1984 | European Pat. Off. | 548/454 |
| 158923 | 10/1985 | European Pat. Off. | 548/454 |

OTHER PUBLICATIONS

J. Cherqui, Chem. Abst., vol. 94, No. 15713z (1977).
J. Cherqui, Chem. Abst., vol. 96, No. 122783k (1981).
L. Unger et al., Chem. Abst., vol. 108, No. 75002j (1987).
J. Diamond et al., Chem. Abst., vol. 79, No. 126115r (1973).
H. Yale, J. Med. and Pharm. Chem., vol. I, No. 2 (1959), pp. 121-131.
A. Burger, Medicinal Chemistry, Third Edition, Part I, p. 71 (1970).

Primary Examiner—Mary E. Ceperley
Attorney, Agent, or Firm—Walter Patton

[57] ABSTRACT

Disclosed herein are novel benzopyrans having pharmacological activity, to a process for preparing them, to pharmaceutical compositions containing them, and to their use in the treatment of hypertension.

6 Claims, No Drawings

NOVEL ANTIHYPERTENSIVE BENZOPYRAN DERIVATIVES

This is a continuation-in-part of copending U.S. Ser. No. 146,875, filed Jan. 22, 1988, now abandoned.

BACKGROUND OF THE INVENTION

The present invention relates to novel benzopyrans having pharmacological activity, to a process for preparing them, to pharmaceutical compositions containing them, and to their use in the treatment of hypertension.

European Patent Publication 158,923 discloses classes of chromans that are described as having blood pressure lowering activity.

The present invention discloses compounds represented by formula (I)

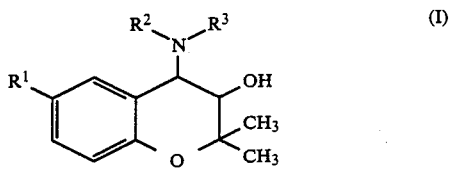

wherein $R^1$ is trifluoromethoxy or $\beta,\beta,\beta$-trifluoroethoxy; $R^2$ and $R^3$ are independently selected from the group consisting of hydrogen, lower alkyl containing 1 to 5 carbon atoms, cyclo lower alkyl containing 5 to 8 carbon atoms,

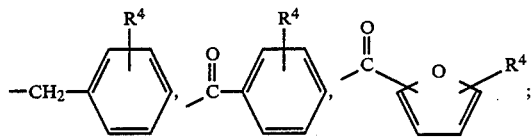

or $R^2$ and $R^3$ are joined to form $+CH_2\frac{}{)n}$ wherein n is 4 to 7; or $R^2$ and $R^3$ are joined together to form

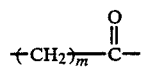

wherein m is 3 to 6; or $R^2$ and $R^3$ are joined together to form

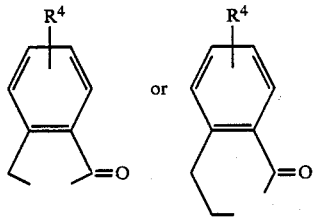

wherein $R^4$ is selected from the group consisting of hydrogen, alkoxy containing 1 to 5 carbon atoms, amino or mono- or disubstituted alkyl amino wherein said alkyl groups contain 1 to 5 carbon atoms and the pharmaceutically acceptable salts and solvates thereof.

A preferred aspect of the present invention are compounds of formula (I) wherein $R^1$ is trifluoromethoxy and $R^2$ and $R^3$ are joined to form

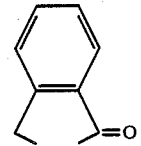

The compounds of formula (I), are asymmetric and, therefore, can exist in the form of optical isomers. The present invention extends to all such isomers individually and as mixtures, such as racemic modifications.

Preferably, a compound of formula (I) is in substantially pure form.

Examples of compounds of formula (I) include the compounds prepared in the Examples hereinafter.

The present invention also provides a process for the preparation of a compound of formula (I), which comprises the reaction of a compound of formula (II)

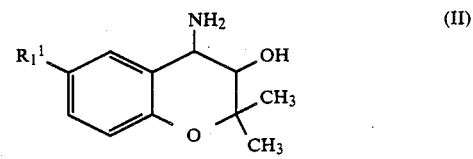

wherein $R_1{}^1$ is $R^1$ as defined hereinbefore or a group or atom convertible thereto, with a compound of formula (III)

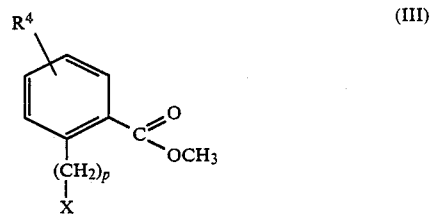

wherein X is chlorine, bromine, or iodine; $R^4$ is as defined above; and p is 1 or 2.

It is particularly preferred that the reaction between the compounds of formula (II) and (III) is carried out under alkylation conditions so as to facilitate the formation of the desired bonds, for example, by heating in the presence of potassium carbonate.

Examples of conversions of a group or atom from $R_1{}^1$ into $R^1$ are generally known in the art of synthetic chemistry. For example, if it is desired to obtain a compound of formula (I) wherein $R^1$ is a trifluoroethoxy group it is possible to convert a compound of formula (I) wherein $R_1{}^1$ is a hydroxy group or a protected hydroxy group to the desired trifluoroethoxy group by deprotecting the hydroxy group and alkylating the hydroxy group in a conventional manner. Examples of protecting agents and their addition and removal are generally known in the art.

The compounds of this invention are capable of forming acid addition salts with therapeutically acceptable acids. The acid addition salts are prepared by reacting the base form of the appropriate compound of formula (I) with one or more equivalents, preferably with an excess, of the appropriate acid in an organic solvent, for example, diethyl ether or an ethanol diethyl ether mixture.

These salts, when administered to a mammal, possess the same or improved pharmacologic activities as the corresponding bases. For many purposes it is preferable to administer the salts rather than the basic compounds. Suitable acids to form these salts include the common mineral acids, e.g. hydrohalic, sulfuric or phosphoric acid; the organic acids, e.g. ascorbic, citric, lactic, aspartic or tartaric acid; and acids which are sparingly soluble in body fluids and which impart slow-release properties to their respective salts, e.g. pamoic or tannic acid or carboxymethyl cellulose. The preferred salt is the hydrochloride salt. The addition salts thus obtained are the functional equivalent of the parent base compound in respect to their therapeutic use. Hence, these addition salts are included within the scope of this invention and are limited only by the requirement that the acids employed in forming the salts be therapeutically acceptable.

The compounds of formula (II) are novel compounds and can be prepared in accordance with the processes described herein.

The compounds of formula (III) are known compounds or can be prepared by conventional procedures from known compounds.

As mentioned previously, the compounds of formula (I) have been found to have blood-pressure lowering activity. They are therefore useful in the treatment of hypertension.

The present invention accordingly provides a pharmaceutical composition which comprises a compound of this invention and a pharmaceutically acceptable carrier. In particular, the present invention provides an anti-hypertensive pharmaceutical composition which comprises an antihypertensive effective amount of a compound of this invention and a pharmaceutically acceptable carrier.

The compositions are preferably adapted for oral administration. However, they may be adapted for other modes of administration, for example parenteral administration for patients suffering from heart failure.

In order to obtain consistency of administration it is preferred that a composition of the invention is in the form of a unit dose. Suitable unit dose forms include tablets, capsules and powders in sachets or vials. Such unit dose forms may contain from 0.1 to 100 mg of a compound of the invention and preferably from 2 to 50 mg. Still further preferred unit dosage forms contain 5 to 25 mg of a compound of the present invention. The compounds of the present invention can be administered orally at a dose range of about 0.01 to 100 mg/kg or preferably at a dose range of 0.1 to 10 mg/kg. Such compositions may be administered from 1 to 6 times a day, more usually from 1 to 4 times a day.

The compositions of the invention may be formulated with conventional excipients, such as a filler, a disintegrating agent, a binder, a lubricant, a flavouring agent and the like. They are formulated in conventional manner, for example in a manner similar to that used for known antihypertensive agents, diuretics and β-blocking agents.

The present invention further provides a compound of the invention for use as an active therapeutic substance. Compounds of formula (I) are of particular use in the treatment of hypertension.

The present invention further provides a method of treating hypertension in mammals including man, which comprises administering to the afflicted mammal an antihypertensive effective amount of a compound or a pharmaceutical composition of the invention.

Synthetic Process A relates to the preparation of a compound of formula (I)

Synthetic Process A

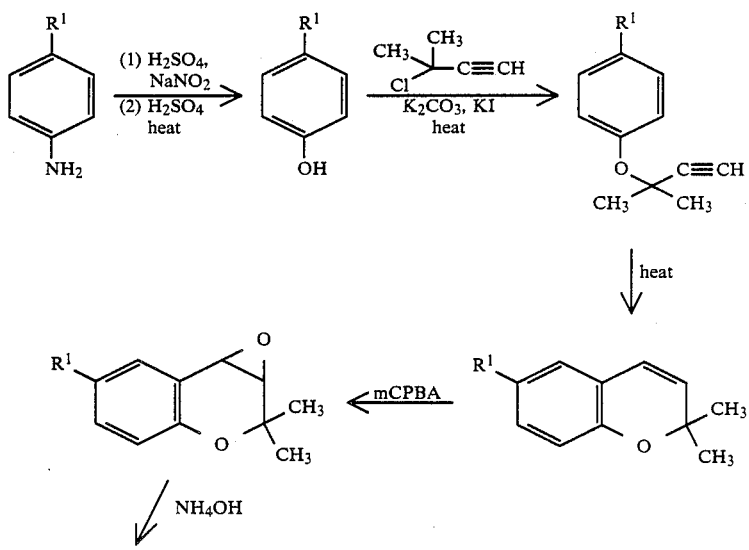

Synthetic Process A

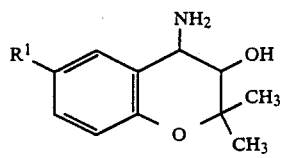

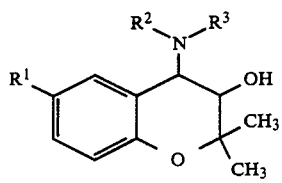

wherein when $R^2$ is hydrogen $R^3$ is benzoyl, furoyl or $R^2$ and $R^3$ are joined to form isoquinolone or isoindolone

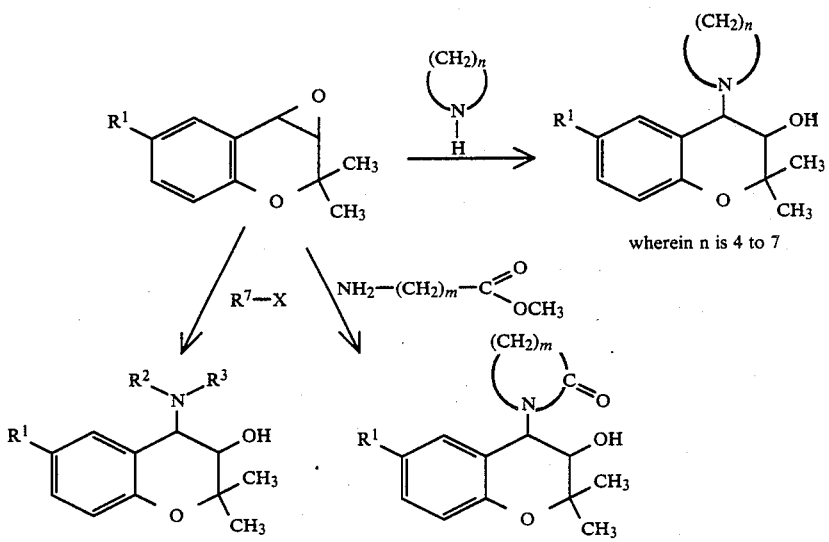

wherein n is 4 to 7 wherein $R^2$ is hydrogen $R^3$ is lower alkyl containing 1 to 5 carbon atoms, cyclo lower alkyl containing 5 to 8 carbon atoms or benzyl wherein m is 3 to 6

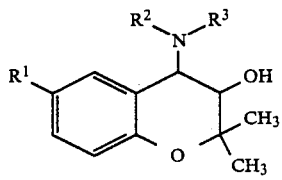

wherein $R^2$ is benzoyl or furoyl and $R^3$ is lower alkyl containing 1 to 5 carbon atoms, cyclo lower alkyl containing 5 to 8 carbon atoms or benzyl wherein $R^1$ is as defined above; X is chlorine, bromine or iodine; $R^6$ is benzoyl, furoyl, or The production of preferred compounds of the present invention is illustrated by Synthetic Process B.

Synthetic Process B

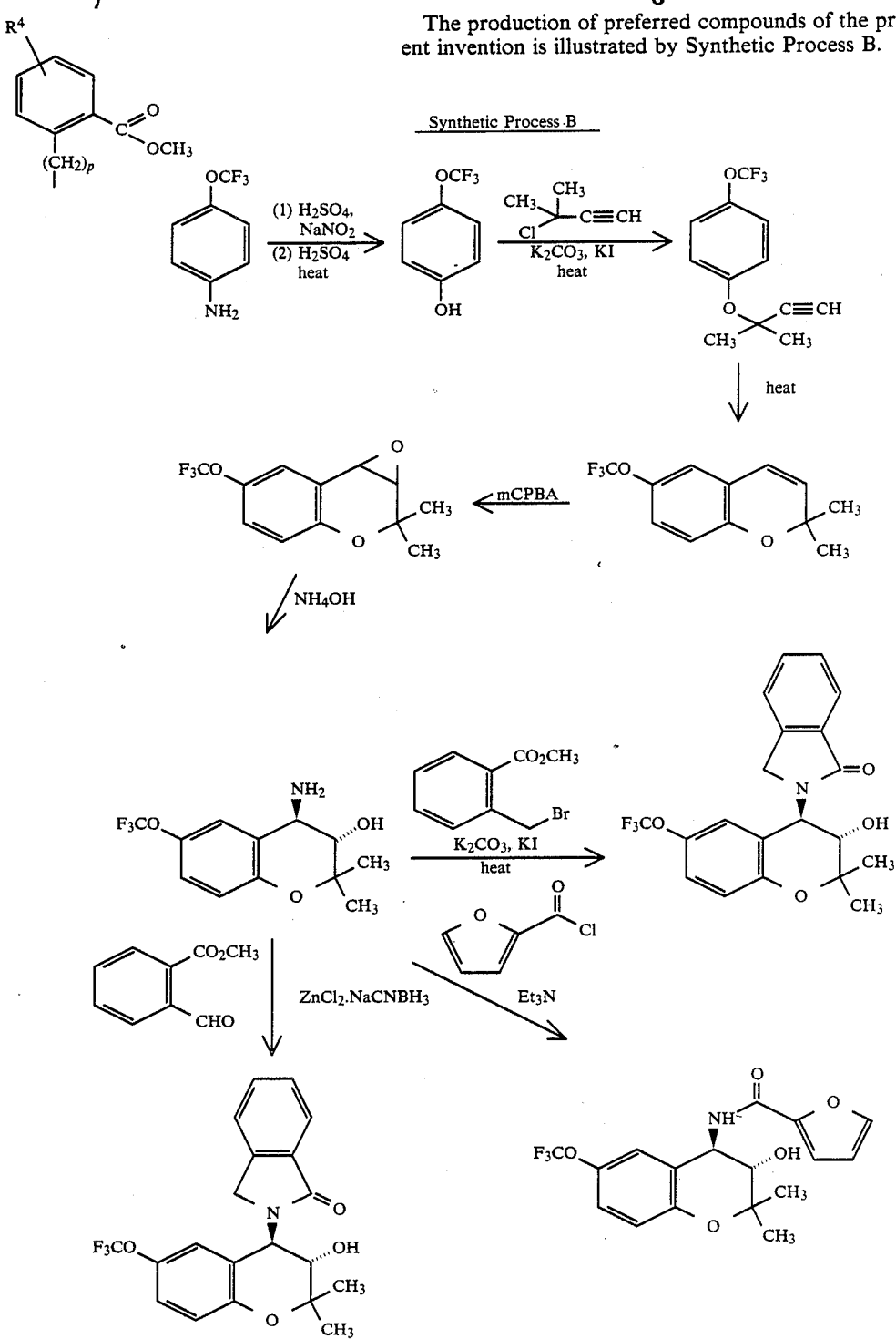

wherein p is 1 or 2; $R^7$ is lower alkyl containing 1 to 5 carbon atoms, cyclo lower alkyl containing 5 to 8 carbon atoms, or benzyl; $R^8$ is benzoyl or furoyl; and $R^4$ is as defined above.

The resolution of compounds of formula (I) into optical isomers may be accomplished by reacting the racemate with an optically pure chiral auxiliary, preferably 1-(1-naphthyl)ethyl isocyanate or α-methylbenzyl isocyanate, to form a mixture of two diastereomers. These diastereomers are then separated by physical means, such as chromatography or crystallization. Each is reacted to remove the chiral auxiliary to afford the enantiomers of compounds of formula (I).

Synthetic Process C relates to the resolution of a preferred compound of formula (I).

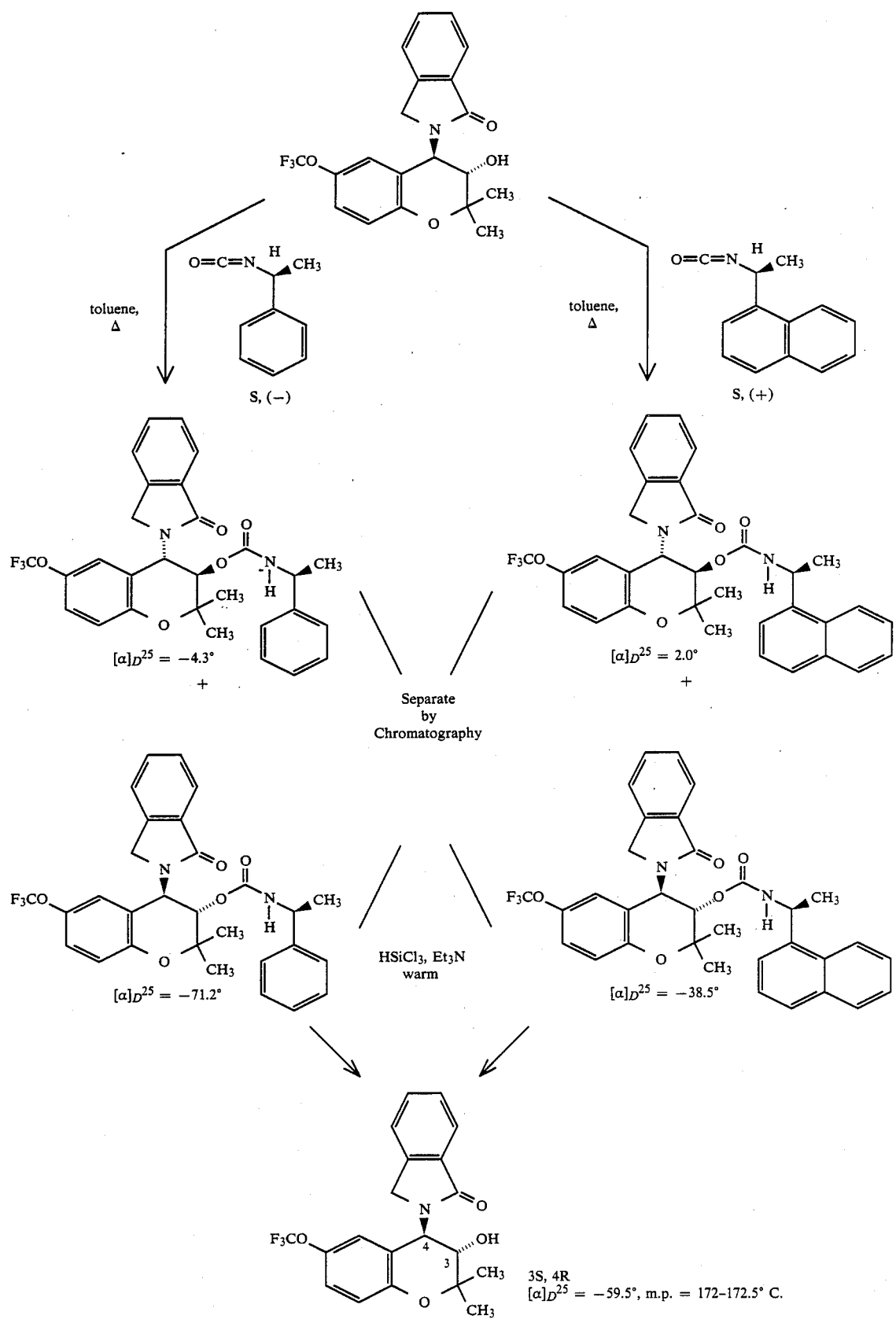

The following Examples further illustrate this invention.

EXAMPLE 1

Preparation of p-Trifluoromethoxy Phenol p-Trifluoromethoxy aniline (49.60 g) was added rapidly dropwise to vigorously stirred 9N aqueous $H_2SO_4$ (500 mL) at 40° C. The mixture was heated to dissolve the solid, then cooled to 0° C. To the fine white suspension, a solution of sodium nitrite (19.46 g in 50 mL of $H_2O$) was added portionwise until an immediate positive KI/starch test result was obtained. This cold solution of diazonium salt was added rapidly dropwise to 9N aqueous $H_2SO_4$ (500 mL) at 110° C. Stirring and heating was continued for 2.5 hours. The mixture was cooled to 10° C. and extracted with diethyl ether (3×500 mL). The combined organic layers were dried (MgSO$_4$), filtered and evaporated in vacuo, then flash chromatographed on $SiO_2$ using diethyl ether as eluant to give 35.0 g of the desired phenol as a light brown oil. The oil was distilled (b.p.=75°–80° C. at 20 torr.) to afford a yellow liquid.

NMR (CDCl$_3$): δ 5.06(1H, s), 6.83(2H, d, J=9.2), 7.11(2H, d, J=9.2 Hz)

EXAMPLE 2

Preparation of 1-[(1,1-Dimethyl-2-propynyl)oxy]-4-(trifluoromethoxy)benzene

To a solution of p-trifluoromethoxy phenol (30.69 g), and 2-methyl-2-chloro-3-butyne (53.00 g) in dry acetonitrile (350 mL) was added potassium iodide (14.30 g) followed by potassium carbonate (92.25 g). This reaction mixture was heated at 70°–80° C. for four days then cooled to room temperature and filtered through celite. The precipitate was washed with dichloromethane and the washings were added to the acetonitrile. The organics were evaporated in vacuo and the oil was taken up in 250 mL of dichloromethane. The organics were washed with water (2×100 mL) and dilute aqueous sodium thiosulfate (2×100 mL), dried (MgSO$_4$), filtered and evaporated in vacuo to leave a dark brown-orange oil. Flash column chromatography on $SiO_2$ using hexane/Et$_2$O (5/1) afforded 34.73 g of the pure product.

NMR (CDCl$_3$) δ 1.64(6H, s), 2.60(1H, s), 7.05–7.30(4H, m)

EXAMPLE 3

Preparation of 2,2-Dimethyl-6-(trifluoromethoxy)-2H-1-benzopyran

A solution of 1-[(1,1-dimethyl-2-propynyl)oxy]-4-trifluoromethoxybenzene (16.25 g) in 60 mL of quinoline was heated to 175° C. for 2 hours. The solution was cooled to room temperature then ether (250 mL) was added. This mixture was stirred for 15 minutes then decanted from any precipitated tars. The ether solution was washed with 1N aqueous hydrochloric acid (3×200 mL) then water (1×200 mL) and dried (K$_2$CO$_3$). The filtered ether solution was evaporated and flash chromatographed on $SiO_2$ using hexane/ethyl acetate (5/1) as eluant to afford 13.92 g (85%) of the desired bicyclic compound.

Alternate Preparation of 2,2-Dimethyl-6-(trifluoromethoxy)-2H-1-benzopyran

A solution of the 1-[(1,1-dimethyl-2-propynyl)oxy]-4-trifluoromethoxybenzene (29.05 g) in 100 mL of chlorobenzene (b.p.=132° C.) was heated to reflux for 24 hours. The reaction mixture was cooled and the solvent removed in vacuo. The oily residue was flash chromatographed on $SiO_2$ using hexane/ethyl acetate (5/1) as eluant to afford 19.72 g of the desired bicyclic compound.

NMR (CDCl$_3$) δ 1.42 (6H, s), 5.67 (1H, d, J=10 Hz), 6.28 (1H, d, J=10 Hz), 6.78 (1H, d, J=5.5 Hz), 6.83 (1H, d, J=2H), 6.94 (1H, dd, J=5.5 Hz, 2 Hz)

EXAMPLE 4

Preparation of 1a,7b-Dihydro-2,2-dimethyl-6-(trifluoromethoxy)-2H-oxireno[c][1]benzopyran To a solution of 2,2-dimethyl-6-trifluoromethoxy-2H-1-benzopyran (14.37 g) in dichloromethane (40 mL) at 0° C. was added a solution of m-chloroperoxybenzoic acid (mCPBA) (14.22 g) in dichloromethane (160 mL) dropwise. After the addition was complete the ice bath was removed and the temperature allowed to warm slowly to 15° C. whilst stirring for 18 hours. The reaction mixture was filtered, and the precipitate was washed with dichloromethane (50 mL). The combined filtrate was washed with 25% aqueous sodium thiosulfate (2×100 mL), and 50% aqueous sodium bicarbonate (2×100 mL), dried (MgSO$_4$), filtered and evaporated in vacuo. The orange oil was flash chromatographed on $SiO_2$ using hexane/ether (4/1) as eluant to afford 13.36 g of the epoxide as a light yellow oil, which solidified upon standing.

NMR (CDCl$_3$) δ 1.25 (3H, s), 1.58 (3H, s), 3.49 (1H, d, J=4 Hz), 3.86 (1H, d, J=4 Hz), 6.78 (1H, d, J=8.5 Hz), 7.11 (1H, dd, J=8.5 Hz and 2 Hz), 7.22 (1H, d, J=2 Hz)

EXAMPLE 5

Preparation of trans-2,3-Dihydro-2,2-dimethyl-3-hydroxy-6-(trifluoromethoxy)-2H-1-benzopyran-4-amine To a solution of 1a,7b-dihydro-2,2-dimethyl-6-(trifluoromethoxy)-2H-oxireno[c][1]benzopyran (6.18 g) in absolute ethanol (30 mL) at 0° C. was added ammonium hydroxide (45 mL). The reaction mixture was capped with a rubber septum and stirred for four days. The reaction mixture was evaporated in vacuo to remove ethanol and water and the oil was taken up in dichloromethane, dried (Na$_2$SO$_4$) filtered and concentrated in vacuo. The residue was flash chromatographed on $SiO_2$ using dichloromethane/methanol (5/1) as eluant to afford the amino-alcohol, m.p. 176°–182° C. (dec.) recrystallized from chloroform.

Two of the above reactions were run simultaneously to obtain 8.95 g of product.

NMR (DMSO-d$_6$) δ 1.07 (3H, s), 1.35 (3H, s), 3.20 (1H, d, J=9.2 Hz), 3.52 (1H, d, J=9.2 Hz), 6.76 (1H, d, J=9 Hz), 7.08 (1H, dd, J=9 Hz, 1.5 Hz), 7.51 (1H, d, J=1.5 Hz)

EXAMPLE 6

Preparation of trans-2-[2,3-Dihydro-2,2-dimethyl-3-hydroxy-6-(trifluoromethoxy)-4H-1-benzopyran-4-yl]-2,3-dihydro-1H-isoindol-1-one To a solution of trans-2,3-dihydro-2,2-dimethyl-3-hydroxy-6-(trifluoromethoxy)-2H-1-benzopyran-4-amine (13.86 g) and methyl 2-formylbenzoate (9.03 g) in 200 mL of dry methanol was added 120 mL of a 0.5 molar solution of zinc chloride-sodium cyanoborohydride (0.06 moles each) in dry methanol. After one hour the mixture was warmed to 50°–55° C. and held there with stirring for 14 hours.

The cooled reaction mixture was quenched with 120 mL of saturated aqueous sodium bicarbonate and the methanol was removed in vacuo. 120 mL of water was added to the residue which was then extracted with dichloromethane (3×200 mL). The combined extracts were washed with water (2×300 mL), dried over $K_2CO_3$, filtered then evaporated to leave an off-white solid.

This solid was dissolved in 500 mL of hot toluene; the mixture was then heated to reflux for 4 to 5 hours. The solution was then cooled and a white precipitate began to form. The mixture was cooled to 0° C. for 0.5 hours during which time a thick mass of white crystals formed. These crystals were collected by vacuum filtration, washed with hexane/toluene (4/1) and dried in vacuo to yield 18.30 g (93%) of analytically pure product as a white flocculent solid, m.p. 212°–213° C.

Alternate Preparation of trans-2-[2,3-Dihydro-2,2-dimethyl-3-hydroxy-6-(trifluoromethoxy)-4H-1-benzopyran-4-yl]-2,3-dihydro-1H-isoindol-1-one To a solution of trans-2,3-dihydro-2,2-dimethyl-3-hydroxy-6-(trifluoromethoxy)-2H-1-benzopyran-4-amine (3.85 g) and methyl 2-bromomethylbenzoate (3.11 g) in dry acetonitrile (80 mL) was added potassium iodide (1.13 g) then potassium carbonate (powdered, 5.63 g). The reaction mixture was stirred under nitrogen at room temperature for 1 hour then heated in a 75°–80° C. oil bath for 24 hours. The cooled mixture was vacuum filtered through celite. The precipitate was washed with ethyl acetate (75 mL), and the filtrates were combined and evaporated. The residue was taken up in ethyl acetate (175 mL), washed with water (2×100 mL) then 25% aqueous sodium thiosulfate (2×100 mL), dried ($MgSO_4$), filtered and evaporated in vacuo. The resultant oil was crystallized from dichloromethane/ethyl acetate (5/1). The crystals were collected, washed with ether, and dried in vacuo to afford the desired compound in 48% yield, m.p. 212°–213° C.

NMR (DMSO-$d_6$) δ 1.24 (3H, s), 1.46 (3H, s), 3.91 (1H, br), 4.06 (1H, br d), 4.48 (1H, br d), 5.24 (1H, br s), 5.77 (1H, d, J=5.8 Hz), 6.70 (1H, br s), 6.92 (1H, d, J=8.9 Hz), 7.17 (1H, dd, J=8.9 Hz and 2.6 Hz), 7.50–7.66 (3H, m), 7.78 (1H, d, J=7.5 Hz)

Anal. Calcd.: C, 61.07; H, 4.61; N, 3.56; Found: C, 60.92; H, 4.87; N, 3.35.

EXAMPLE 7

Preparation of trans-N-[2,3-Dihydro-2,2-dimethyl-3-hydroxy-6-(trifluoromethoxy)-4H-1-benzopyran-4-yl]-2-furancarboxamide To a solution of trans-2,3-dihydro-2,2-dimethyl-3-hydroxy-6-(trifluoromethoxy)-2H-1-benzopyran-1-benzopyran-4-amine (3.40 g) and triethylamine (1.84 mL) in dichloromethane (60 mL) at 5° C. was added 2-furoyl chloride (1.30 mL) dropwise via a pipet. After 10 minutes the ice water bath was removed and the reaction was stirred and allowed to raise to ambient temperature. TLC at 2.5 hours indicated complete reaction and the mixture was increased in volume by adding 60 mL of dichloromethane. The organics were washed with 0.1N aqueous HCl (2×80 mL), 50% aqueous sodium bicarbonate (2×80 mL) and water (1×80 mL), dried ($MgSO_4$), filtered and evaporated in vacuo. The oily residue was flash chromatographed on $SiO_2$ using dichloromethane/ethyl acetate (8/1) as eluant to leave a colorless oil. The desired compound was crystallized from ether/hexane (1/1) to give white needles, m.p. 146°–147° C. yield 50%.

NMR (DMSO-$d_6$) δ 1.16 (3H, s), 1.39 (3H, s), 3.74 (1H, dd, J=5.9 Hz and 9.8 Hz), 4.96 (1H, t, J=9.3 Hz), 5.65 (1H, d, J=6 Hz), 6.64 (1H, m), 6.86 (1H, d, J=9 Hz), 6.93 (1H, d, J=2.6 Hz), 7.14 (1H, dd, J=9 Hz and 2.6 Hz), 7.17 (1H, d, J=2.6 Hz), 7.86 (1H, s), 8.73 (1H, d, J=9 Hz).

Anal. Calcd.: C, 54.99; H, 4.34; N, 3.77; Found: C, 54.79; H, 4.67; N, 3.71.

The following Examples illustrate the resolution of the compounds of this invention into optical isomers.

EXAMPLE 8

Preparation of (+)- and (−)-(trans)-[1-(1-naphthalenyl)ethyl]carbamic Acid 4-(1,3-Dihydro-1-oxo-2H-isoindol-2-yl)-3,4-dihydro-2,2-dimethyl-6-(trifluoromethoxy)-2H-1-benzopyran-3-yl Ester A solution of trans-2-[2,3-dihydro-2,2-dimethyl-3-hydroxy-6-(trifluoromethoxy)-4H-1-benzopyran-4-yl]-2,3-dihydro-1H-isoindol-1-one (8.53 g) and S-(+)-1-(1-naphthyl)ethyl isocyanate (5.15 g) in dry toluene (275 mL) was heated at 110°–115° C. for 24 hours. The cooled mixture was evaporated in vacuo, then flash chromatographed on silica gel (1 kg) using dichloromethane/hexane/ethyl acetate (6/6/1) as eluant to afford the following: (a) 4.74 g of diastereomer A, (b) 3.75 g of a mixture of both diastereomers and (c) 4.20 g of diastereomer B.

Pure diastereomer (A): glass, $[\alpha]_D^{25} = +2.0$, c=1, $CHCl_3$

NMR ($CDCl_3$): δ 1.25 (3H, d), 1.33 (3H, s), 1.42 (3H, s), 4.09 (1H, AB d, J=16.4 Hz), 4.59 (1H, AB, d, J=16.4 Hz), 5.12 (NH, d, J=8.2 Hz), 5.20 (1H, d, J=10.5 Hz), 5.33 (1H, m), 5.76 (1H, d, J=10.5 Hz), 6.78 (1H, d, J=3.0 Hz), 6.88 (1H, d, J=8.9 Hz), 7.07 (1H, dd, J=8.9 Hz and 3.0 Hz), 7.38–7.60 (7H, m) and 7.70–8.00 (4H, m)

Pure diastereomer (B): glass, $[\alpha]_D^{25} = -38.0°$, c=1, $CHCl_3$

NMR ($CDCl_3$): δ 1.40 (3H, s), 1.51 (3H, s), 1.53 (3H, d, J=7.0 Hz), 3.96 (1H, AB d, J=16.3 Hz), 4.40 (1H, AB d, J=16.3 Hz), 5.23 (1H, d, J=10.6 Hz), 5.25 (NH, d), 5.39 (1H, m), 5.76 (1H, d, J=10.6 Hz) and 6.68–7.87 (14H, series of m)

In addition, this experiment was repeated using S—(—)— α-methylbenzyl isocyanate as the chiral auxiliary. The purified and separated diastereomers were crystallized by diffusion of hexane into an ethyl acetate solution.

EXAMPLE 9

Preparation of (−)-3S,4R-trans-2-[2,3-Dihydro-2,2-dimethyl-3-hydroxy-6-(trifluoromethoxy)-4H-1-benzopyran-4-yl]-2,3-dihydro-1H-isoindol-1-one To a solution of (−)-(trans)-[1-(1-naphthalenyl)ethyl]carbamic acid 4-(1,3-dihydro-1-oxo-2H-isoindol-2-yl)-3,4-dihydro-2,2-dimethyl-6-(trifluoromethoxy)-2H-1-benzopyran-3-yl ester, diastereomer B, (5.86 g) in dichloromethane (150 mL) at room temperature was added triethylamine (3.49 mL) followed by the dropwise addition of trichlorosilane (2.53 mL). This mixture was stirred at room temperature for 6 hours then warmed to 40° C. for 18 hours. The cooled mixture was quenched with 140 mL of 2M aqueous ammonium hydroxide. This mixture was stirred for 30 minutes. Celite was added to the mixture and then it was filtered. The precipitate was placed into a flask and washed with good agitation with dichloromethane (100 mL). This mixture was filtered and the filtrates were combined in a separatory funnel. The organic layer was washed with water, dried ($K_2CO_3$) and evaporated in vacuo. The residue was flash chromatographed on silica gel using ethyl ether/hexane (4/1) as eluant. The desired product was crystallized from hot hexane/ethyl ether (2/1), m.p. 172°–172.5° C.

$[\alpha]_D^{25} = -59.50°$, c=1, $CHCl_3$

The NMR of this product is substantively the same as for the product of Example 6.

Pharmacological Data

Male Okamoto-Aoki spontaneously hypertensive rats (SHR) ranging in weight from 250–400 g were anesthetized with halothane. Their left femoral arteries and veins were cannulated with polyethylene tubing of the appropriate size (i.d. 0.023″, o.d. 0.038″). Each animal was placed in a Bollman cage, and the tail, along with two cannulas, was extended through a hole in one end of the cage. The tail was taped securely to a firm rubber board to prevent the rat from turning in its cage to dislodge the cannulas. The femoral arterial cannula was connected to a Statham pressure transducer which in turn was attached to a polygraph for recording arterial pressure and pulse rate. The pulse rate was considered to be the heart rate.

After the blood pressure has stabilized (usually 2 hours after cessation of the anesthesia), standard agonists were injected by the i.v. route. The doses administered were: isoproterenol 0.5 μg/kg, adrenaline 2.0 μg/kg, tyramine 200 μg/kg and angiotensin-I 0.25 μg/kg. The agonists were given in random order except that tyramine was never preceded by isoproterenol as the response to tyramine seemed to be blunted after a prior injection of isoproterenol. Enough time was allowed for the BP to return to preinjection levels before the test compound was administered by gastric lavage. The time of drug administration was designated as time zero. Heart rate and blood pressure were recorded at 5, 10, 15, 30, 45 and 60 minutes and hourly thereafter for a period of 4 hours after drug administration. At 1 and 2 hours post-drug the agonists were again injected at the same concentration and in the same order as during the control period.

For each compound the maximum mean fall in blood pressure was compared to pretreatment control values and expressed as a percentage fall in blood pressure.

Blood Pressure Lowering by Compound of Formula (I)

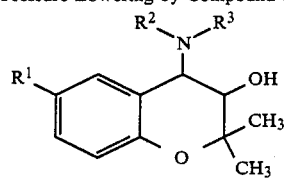

(I)

| $R^1$ | $R^2$ and $R^3$ | mg/kg p.o. | n | Pre-treat. MABP mm Hg | Max Δ BP mm Hg | % | Pre-treat. HR beats/ min. | Max Δ HR beats | % |
|---|---|---|---|---|---|---|---|---|---|
| $CF_3O-$ | racemate | 10 | 3 | 178 | −93 at 4 Hr | −52 | 351 | +87 at 4 Hr | +25 |
|  |  | 0.5 | 4 | 181 | −56 at 4 Hr | −31 | 364 | +89 at 4 Hr | +24 |
|  | 3S, 4R enantiomer | 0.05 | 6 | 183 | −13 at 3 Hr | −7 | 415 | −11 at 3 Hr | −3 |
|  |  | 0.13 | 8 | 178 | −35 at 2 Hr | −20 | 369 | +34 at 2 Hr | +9 |
|  |  | 0.25 | 10 | 172 | −49 at 1 Hr<br>−48 at 5 Hr | −29<br>−28 | 378 | +65 at 1 Hr | +17 |
|  |  | 0.5 | 8 | 180 | −75 at 45 min<br>−75 at 5 Hr | −42<br>−42 | 402 | +75 at 45 min<br>+49 at 5 Hr | +19<br>+12 |

-continued

Blood Pressure Lowering by Compound of Formula (I)

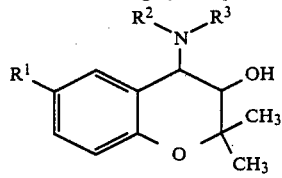
(I)

| R₁ | R₂ | R₃ | mg/kg p.o. | n | Blood Pressure | | | Heart Rate | | |
|---|---|---|---|---|---|---|---|---|---|---|
| | | | | | Pre-treat. MABP mm Hg | Max Δ BP mm Hg | % | Pre-treat. HR beats/min. | Max Δ HR beats | % |
| CF₃O— | ![furoyl] | —H | 10 | 4 | 176 | −96 at 30 min | −55 | 423 | +57 at 30 min | +13 |
| | Control | | 0 | 6 | 172 | −5 at 3 Hr | −3 | 372 | +21 at 4 Hr | +6 |

Compounds of formula (I) may be administered alone or with a diuretic, such as hydrochlorothianzide, or a β-blocker, such as propranolol or cetamolol in a suitable unit dose form.

We claim:

1. A compound of formula (I)

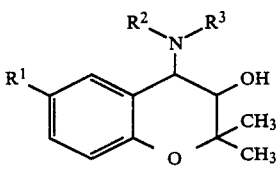
(I)

wherein R¹ is trifluoromethoxy or β,β,β-trifluoroethoxy; R² and R³ are independently selected from the group consisting of hydrogen, lower alkyl containing 1 to 5 carbon atoms, cyclo lower alkyl containing 5 to 8 carbon atoms,

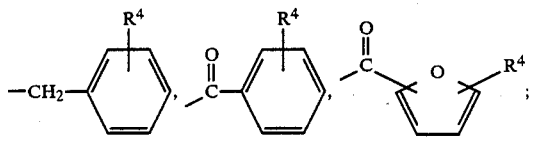

or R² and R³ are joined to form $\text{-(CH}_2\text{)}_n\text{-}$ wherein n is 4 to 7; or R² and R³ are joined together to form

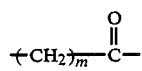

wherein m is 3 to 6; or R² and R³ are joined together to form

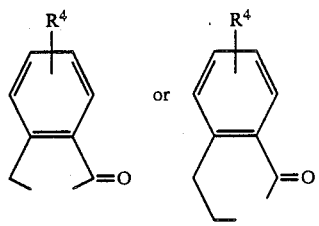

wherein R⁴ is selected from the group consisting of hydrogen, alkoxy containing 1 to 5 carbon atoms, amino or mono- or disubstituted alkyl amino wherein said alkyl groups contain 1 to 5 carbon atoms and the pharmaceutically acceptable salts and solvates thereof.

2. The compound according to claim 1 designated trans-2-[2,3-dihydro-2,2-dimethyl-3-hydroxy-6-(trifluoromethoxy)-4H-1-benzopyran-4-yl]-2,3-dihydro-1H-isoindol-1-one and the pharmaceutically acceptable salts thereof.

3. The compound according to claim 1 designated trans-N-[2,3-dihydro-2,2-dimethyl-3-hydroxy-6-(trifluoromethoxy)-4H-1-benzopyran-4-yl]-2-furancarboxamide and the pharmaceutically acceptable salts thereof.

4. The compound according to claim 2 designated (−)-3S,4R-trans-2-[2,3-dihydro-2,2-dimethyl-3-hydroxy-6-(trifluoromethoxy)-4H-1-benzopyran-4-yl]-2,3-dihydro-1H-isoindol-1-one and the pharmaceutically acceptable salts thereof.

5. A pharmaceutical composition comprising an effective amount of a compound according to claim 1 or a pharmaceutically acceptable salt or solvate thereof and a pharmaceutically acceptable carrier for use in the treatment of hypertension.

6. A method of treatment of hypertension in mammals which comprises administering to the mammal in need thereof an effective antihypertensive amount of a compound of formula (I) according to claim 1.

* * * * *